(12) United States Patent
Yanagidate

(10) Patent No.: US 9,485,428 B2
(45) Date of Patent: Nov. 1, 2016

(54) IMAGE TRANSMISSION DEVICE AND IMAGING DISPLAY SYSTEM

(71) Applicant: OLYMPUS CORPORATION, Tokyo (JP)

(72) Inventor: Masaharu Yanagidate, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 121 days.

(21) Appl. No.: 14/073,314

(22) Filed: Nov. 6, 2013

(65) Prior Publication Data

US 2014/0063284 A1  Mar. 6, 2014

Related U.S. Application Data

(63) Continuation of application No. PCT/JP2012/061805, filed on May 9, 2012.

(30) Foreign Application Priority Data

May 12, 2011  (JP) ................................. 2011-107561

(51) Int. Cl.
*H04N 5/232* (2006.01)
*H04N 5/225* (2006.01)
*H04N 7/18* (2006.01)
(Continued)

(52) U.S. Cl.
CPC .......... *H04N 5/23293* (2013.01); *H04N 5/225* (2013.01); *H04N 5/23216* (2013.01); *H04N 7/185* (2013.01); *H04N 9/69* (2013.01); *A61B 1/00009* (2013.01); *A61B 1/00016* (2013.01)

(58) Field of Classification Search
CPC ............. H04N 5/232; H04N 5/23216; H04N 5/23293; H04N 5/225; H04N 5/23229
See application file for complete search history.

(56) References Cited

U.S. PATENT DOCUMENTS

| 6,243,133 | B1 | 6/2001 | Spaulding et al. |
| 6,466,334 | B1 * | 10/2002 | Komiya ................. H04N 1/603 358/1.9 |
| 6,654,491 | B1 * | 11/2003 | Hidaka .................... G09G 5/02 358/516 |

(Continued)

FOREIGN PATENT DOCUMENTS

| EP | 1207463 A2 | 5/2002 |
| JP | 2001-320616 A | 11/2001 |

(Continued)

OTHER PUBLICATIONS

Extended European Search Report dated Sep. 19, 2014, issued in corresponding European Application No. 12782090.0. (5 pages).

(Continued)

*Primary Examiner* — Abdelaaziz Tissire
(74) *Attorney, Agent, or Firm* — Westerman, Hattori, Daniels & Adrian, LLP

(57) ABSTRACT

An image transmission device is an image transmission device in an imaging display system in which an imaging device which images a subject and outputs frame image data, the image transmission device which wirelessly transmits the frame image data, an image reception device which wirelessly receives the wirelessly transmitted frame image data, and a display device which displays an image thereon based on the frame image data wirelessly received by the image reception device are included. The image transmission device includes an input unit, an image processing unit, a communication unit, and an adjustment unit.

6 Claims, 14 Drawing Sheets

(51) Int. Cl.
*H04N 9/69* (2006.01)
*A61B 1/00* (2006.01)

(56) References Cited

U.S. PATENT DOCUMENTS

| | | | | |
|---|---|---|---|---|
| 6,667,765 | B1* | 12/2003 | Tanaka | H04N 5/2353 348/229.1 |
| 7,009,640 | B1* | 3/2006 | Ishii | G06T 7/408 348/223.1 |
| 2001/0009438 | A1 | 7/2001 | Kihara et al. | |
| 2001/0019365 | A1* | 9/2001 | Kim | H04N 5/4401 348/554 |
| 2002/0036645 | A1* | 3/2002 | Funahashi | A61B 6/461 345/596 |
| 2002/0101514 | A1* | 8/2002 | Watanabe | H04L 12/40058 348/211.4 |
| 2002/0118958 | A1* | 8/2002 | Ishikawa | H04N 5/073 386/223 |
| 2002/0120781 | A1* | 8/2002 | Hirashima | G06F 3/14 709/246 |
| 2003/0016289 | A1* | 1/2003 | Motomura | H04N 1/46 348/211.5 |
| 2003/0177241 | A1* | 9/2003 | Katayama | G06F 11/3495 709/226 |
| 2004/0183915 | A1* | 9/2004 | Gotohda | H04N 5/23206 348/207.11 |
| 2005/0100136 | A1 | 5/2005 | Kawatsu | |
| 2006/0132656 | A1* | 6/2006 | Yamamoto | H04N 5/4403 348/571 |
| 2007/0097223 | A1* | 5/2007 | Ono | H04N 5/232 348/211.99 |
| 2007/0126875 | A1* | 6/2007 | Miyamaki | G08B 13/19656 348/207.11 |
| 2007/0140579 | A1* | 6/2007 | Miyashita | H04N 9/735 382/254 |
| 2007/0165048 | A1* | 7/2007 | Yamashita | G06T 5/009 345/601 |
| 2008/0122949 | A1* | 5/2008 | Kindborg | G08B 13/19671 348/231.99 |
| 2008/0239157 | A1* | 10/2008 | Rai | G06F 3/1431 348/674 |
| 2009/0147100 | A1 | 6/2009 | Nagamasa et al. | |
| 2013/0057723 | A1* | 3/2013 | Mitsugi | H04N 5/232 348/222.1 |
| 2014/0002625 | A1* | 1/2014 | Yanagidate | H04N 1/33307 348/65 |
| 2014/0015946 | A1* | 1/2014 | Yanagidate | A61B 5/7445 348/65 |
| 2015/0215563 | A1* | 7/2015 | Yanagidate | H04N 5/23206 348/500 |

FOREIGN PATENT DOCUMENTS

| | | |
|---|---|---|
| JP | 2003-125271 A | 4/2003 |
| JP | 2004-140799 A | 5/2004 |
| JP | 2006-304216 A | 11/2006 |
| JP | 2008-017476 A | 1/2008 |

OTHER PUBLICATIONS

International Search Report dated Aug. 7, 2012, issued in corresponding application No. PCT/JP2012/061805.

* cited by examiner

| IMAGING DEVICE | COLOR GAIN | HUE ANGLE | GAMMA | FREQUENCY CHARACTERISTIC (0, 0.1, 0.2, 0.3, 0.4, 0.5) |
|---|---|---|---|---|
| ID_a | 1.1 | 10 | 1/2.2 | (1, 1, 1, 1, 1, 1.2, 1) |
| ID_b | 0.8 | -10 | 1/1.8 | (1, 1, 1, 1.2, 1.3, 1) |
| ⋮ | ⋮ | ⋮ | ⋮ | ⋮ |

| IMAGING DEVICE | COLOR GAIN | HUE ANGLE | GAMMA | FREQUENCY CHARACTERISTIC (0, 0.1, 0.2, 0.3, 0.4, 0.5) |
|---|---|---|---|---|
| ID_a | 1.1 | 10 | 0.45 | (1, 1, 1, 1.1, 1.2, 1) |
| ID_c | 1.2 | 20 | 0.56 | (1, 1, 1, 1.2, 1.2, 1) |
| ⋮ | ⋮ | ⋮ | ⋮ | ⋮ |

FIG. 15

| USER ID | COLOR GAIN | HUE ANGLE | GAMMA | FREQUENCY CHARACTERISTIC (0, 0.1, 0.2, 0.3, 0.4, 0.5) |
|---|---|---|---|---|
| MD1 | 0.9 | 5 | 0.5 | (1, 1, 1, 1, 1.2, 1.1) |
| ⋮ | ⋮ | ⋮ | ⋮ | ⋮ |

FIG. 16

| TRANSMISSION DEVICE | COLOR GAIN | HUE ANGLE | GAMMA | FREQUENCY CHARACTERISTIC (0, 0.1, 0.2, 0.3, 0.4, 0.5) |
|---|---|---|---|---|
| TX_a | 0.82 | −5 | 1.11 | (1, 1, 1, 1, 1, 1.1) |
| TX_c | 0.75 | −15 | 0.89 | (1, 1, 1, 0.83, 1, 1.1) |
| ⋮ | ⋮ | ⋮ | ⋮ | ⋮ |

FIG. 20

| COLOR GAIN | HUE ANGLE | GAMMA | FREQUENCY CHARACTERISTIC (0, 0.1, 0.2, 0.3, 0.4, 0.5) |
|---|---|---|---|
| 1.0 | 0 | 0.45 | (1, 1, 1, 1, 1.2, 1) |

FIG. 21

| TRANSMISSION DEVICE | COLOR GAIN | HUE ANGLE | GAMMA | FREQUENCY CHARACTERISTIC (0, 0.1, 0.2, 0.3, 0.4, 0.5) |
|---|---|---|---|---|
| TX_a | 0.91 | −10 | 1.00 | (1, 1, 1, 1, 1, 1) |
| TX_c | 0.83 | −20 | 0.80 | (1, 1, 1, 0.83, 1, 1) |

FIG. 22

| USER ID | COLOR GAIN | HUE ANGLE | GAMMA | FREQUENCY CHARACTERISTIC (0, 0.1, 0.2, 0.3, 0.4, 0.5) |
|---|---|---|---|---|
| MD1 | 0.9 | 5 | 1.1 | (1, 1, 1, 1, 1.2, 1.1) |
| MD2 | 1.0 | −10 | 1.0 | (1, 1, 1, 1.2, 1.3, 1) |
| ⋮ | ⋮ | ⋮ | ⋮ | ⋮ |

FIG. 23

| MONITOR | COLOR GAIN | HUE ANGLE | GAMMA | FREQUENCY CHARACTERISTIC (0, 0.1, 0.2, 0.3, 0.4, 0.5) |
|---|---|---|---|---|
| DS_e | 0.8 | 0 | 2.2 | (1, 1, 1, 1.2, 1.2, 1) |
| DS_f | 0.9 | 0 | 1.8 | (1, 1, 1, 1, 1.2, 1) |

FIG. 24

| RECEPTION DEVICE | COLOR GAIN | HUE ANGLE | GAMMA | FREQUENCY CHARACTERISTIC (0, 0.1, 0.2, 0.3, 0.4, 0.5) |
|---|---|---|---|---|
| RX_e | 1.13 | 5 | 1.11 | (1, 1, 1, 0.83, 0.83, 1.1) |
| RX_f | 1.11 | −10 | 1.23 | (1, 1, 1, 1.2, 1.1, 1) |

IMAGE TRANSMISSION DEVICE AND IMAGING DISPLAY SYSTEM

This application is a continuation application based on a PCT Patent Application No. PCT/JP2012/061805, filed on May 9, 2012, whose priority is claimed on Japanese Patent Application No. 2011-107561, filed on May 12, 2011. The contents of both the PCT Application and the Japanese Application are incorporated herein by reference.

BACKGROUND OF THE INVENTION

1. Field of the Invention

The present invention relates to an image transmission device that performs image processing on frame image data generated by an imaging device and transmits the data in a wireless manner. In addition, the present invention relates to an imaging display system that includes an imaging device, an image transmission device, an image reception device, and a display device.

2. Description of Related Art

A system in which, when an imaging device images a subject and generates an image to be displayed, desired image processing is performed on the captured image based on an image processing parameter set by a control device, and then the captured image is displayed, has been developed. For example, Japanese Patent Application No. 2003-125271 discloses a method of performing image processing on a captured image in an imaging device (digital camera) according to an image processing parameter transferred from a control device (remote controller), and thereby generating and outputting display data.

In this method, display data suitable for a display device is generated by performing imaging processing on image data. This method is used on the premise that, in a system, the corresponding relationship between an imaging device and a display device is one-to-one. For this reason, this method cannot be applied to a system configured by a plurality of imaging devices in which the quality of displayed images on a display device should be adjusted so as to reduce a difference in imaging characteristics between the imaging devices.

SUMMARY OF THE INVENTION

According to a first aspect of the present invention, an image transmission device is an image transmission device in an imaging display system which includes an imaging device, an image transmission device, an image reception device, and a display device. The imaging device images a subject and outputs frame image data. The image transmission device wirelessly transmits the frame image data. The image reception device wirelessly receives the wirelessly transmitted frame image data. The display device displays an image thereon based on the frame image data wirelessly received by the image reception device. In addition, the image transmission device includes an input unit, an image processing unit, a communication unit, and an adjustment unit. An imaging characteristic parameter of the imaging device and the frame image data may be input to the input unit. The image processing unit may perform image processing on the frame image data input to the input unit based on a processing parameter. The communication unit may wirelessly transmit the frame image data of an image that has been processed by the image processing unit to the image reception device, and wirelessly receive an index parameter, which is used as an index value when the processing parameter is adjusted, so as to reduce a difference in image quality caused by imaging characteristics of each imaging device. The adjustment unit may adjust the processing parameter based on the imaging characteristic parameter and the index parameter.

According to a second aspect of the present invention, the imaging display system according to the first aspect of the present invention includes a first imaging device, an image transmission device, a second imaging device, an image reception device, and a display device. The first imaging device images a subject and outputs first frame image data. The image transmission device wirelessly transmits the first frame image data. The second imaging device images a subject and outputs second frame image data. The image reception device wirelessly receives the wirelessly transmitted first frame image data. The display device displays a first image based on the first frame image data wirelessly received by the image reception device and a second image based on the second frame image data output from the second imaging device thereon. In addition, an imaging characteristic parameter of the first imaging device and the first frame image data may be input to the input unit. The image processing unit may process the first frame image data input to the input unit. The communication unit may wirelessly transmit the first frame image data of an image that has been processed by the image processing unit to the image reception device. Further, the communication unit may wirelessly receive an imaging characteristic parameter of the second imaging device as the index parameter.

According to a third aspect of the present invention, in an image transmission device according to the first aspect of the present invention, the communication unit may wirelessly receive an adjustment target parameter of the quality of an image to be displayed on the display device as the index parameter.

According to a fourth aspect of the present invention, in an image transmission device according to the first aspect of the present invention, the communication unit may wirelessly receive a standard imaging characteristic parameter designated in advance as the index parameter.

According to a fifth aspect of the present invention, in an image transmission device according to the first aspect of the present invention, the communication unit may wirelessly receive the index parameter from the image reception device.

According to a sixth aspect of the present invention, in an image transmission device according to the first aspect of the present invention, the communication unit may wirelessly receive the index parameter from a control device which controls wireless connection of the image transmission device to the image reception device.

According to a seventh aspect of the present invention, in an image transmission device according to the first aspect of the present invention, the imaging characteristic parameter, the processing parameter, and the index parameter may refer to parameter values of a color gain, a hue angle, gamma, and a frequency characteristic.

According to an eighth aspect of the present invention, in an image transmission device according to the first aspect of the present invention, the adjustment unit may adjust the processing parameter based on a value obtained by dividing the index parameter by the imaging characteristic parameter.

According to a ninth aspect of the present invention, an imaging display system includes an imaging device, an image transmission device, an image reception device, and a display device. The imaging device images a subject and outputs frame image data. The image transmission device wirelessly transmits the frame image data. The image reception device wirelessly receives the wirelessly transmitted frame image data. The display device displays an image thereon based on the frame image data wirelessly received by the image reception device. In addition, the image transmission device includes an input unit, an image processing unit, a communication unit, and an adjustment unit. An imaging characteristic parameter of the imaging device and the frame image data may be input to the input unit. The image processing unit may perform image processing on the frame image data input to the input unit based on a processing parameter. The communication unit may wirelessly transmit the frame image data of an image that has been processed by the image processing unit to the image reception device, and wirelessly receive an index parameter, which is used as an index value when the processing parameter is adjusted, so as to reduce a difference in image qualities caused by an imaging characteristic of each imaging device. The adjustment unit adjusts the processing parameter based on the imaging characteristic parameter and the index parameter.

According to a tenth aspect of the present invention, in an imaging display system according to the ninth aspect of the present invention, the imaging display system further includes a control device which controls wireless connection of the image transmission device to the image reception device, and wirelessly transmits the index parameter, which is used as an index value when the processing parameter is adjusted to the image transmission device. The communication unit may receive the index parameter from the control device.

According to an eleventh aspect of the present invention, an imaging display system includes a first imaging device, an image transmission device, a second imaging device, an image reception device, and a display device. The first imaging device images a subject and outputs first frame image data. The image transmission device wirelessly transmits the first frame image data. The second imaging device images a subject and outputs second frame image data. The image reception device wirelessly receives the wirelessly transmitted first frame image data. The display device displays a first image based on the first frame image data wirelessly received by the image reception device and displays a second image based on the second frame image data output from the second imaging device thereon. In addition, the image transmission device includes an input unit, an image processing unit, a first communication unit, and an adjustment unit. An imaging characteristic parameter of the first imaging device and the first frame image data may be input to the input unit. The image processing unit may perform image processing on the first frame image data input to the input unit based on a processing parameter. The first communication unit may wirelessly transmit the first frame image data of an image that has been processed by the image processing unit to the image reception device and wirelessly receive an imaging characteristic parameter of the second imaging device, which is used as an index value when the processing parameter is adjusted, so as to reduce a difference in image qualities caused by imaging characteristics of each of the imaging devices from the image reception device. The adjustment unit may adjust the processing parameter based on the imaging characteristic parameter of the first imaging device and the imaging characteristic parameter of the second imaging device. In addition, the image reception device includes a second communication unit and an output unit. The second communication unit may wirelessly receive the first frame image data from the image transmission device and wirelessly transmit the imaging characteristic parameter of the second imaging device to the image transmission device. The output unit may output the first frame image data.

According to a twelfth aspect of the present invention, an imaging display system includes a plurality of imaging devices, a plurality of image transmission device, an image reception device, and a display device. The plurality of imaging devices image a subject and output frame image data. A plurality of image transmission devices are provided such that there is one corresponding to each of the plurality of imaging devices and each wirelessly transmits the frame image data output from the imaging devices. The image reception device wirelessly receives the wirelessly transmitted frame image data. The display device displays thereon images based on the frame image data wirelessly received by the image reception device. In addition, each of the image transmission devices includes an input unit, an image processing unit, a first communication unit, and an adjustment unit. Imaging characteristic parameters of the imaging devices and the frame image data may be input to the input unit. The image processing unit may perform image processing on the frame image data input to the input unit based on a processing parameter. The first communication unit may wirelessly transmit the frame image data of an image that has been processed by the image processing unit to the image reception device and wirelessly receive an adjustment target parameter of the quality of images, which is used as an index value to be displayed on the display device when the processing parameter is adjusted, so as to reduce a difference in image qualities caused by imaging characteristics of each of the imaging devices from the image reception device. The adjustment unit may adjust the processing parameter based on the imaging characteristic parameters of the imaging devices and the adjustment target parameter. In addition, the image reception device includes a second communication unit and an output unit. The second communication unit may wirelessly receive the frame image data from the image transmission devices and wirelessly transmit the adjustment target parameter to the image transmission devices. The output unit may output the frame image data.

According to an thirteenth aspect of the present invention, the imaging display system includes a plurality of imaging devices, a plurality of image transmission device, an image reception device, a display device, and a control device. The plurality of imaging devices image a subject and output frame image data. The plurality of image transmission devices are provided such that there is one corresponding to each of the plurality of imaging devices and each wirelessly transmits the frame image data output from the imaging devices. The image reception device wirelessly receives the wirelessly transmitted frame image data. The display device displays thereon images based on the frame image data wirelessly received by the image reception device. The control device controls wireless connection of the image transmission devices to the image reception device and wirelessly transmit a standard imaging characteristic parameter designated in advance, which is used as an index value when a processing parameter is adjusted, so as to reduce a difference in image qualities caused by imaging characteristics of each of the imaging devices to the image transmission devices. In addition, each of the image transmission devices includes an input unit, an image processing unit, a first communication unit, and an adjustment unit. Imaging characteristic parameters of the imaging devices and the frame image data may be input to the input unit. The image processing unit may perform image processing on the frame image data input to the input unit based on the processing parameter. The first communication unit may wirelessly transmit the frame image data of an image that has been processed by the image processing unit to the image reception device and wirelessly receive the standard imaging characteristic parameter from the control device. The adjustment unit may adjust the processing parameter based on the imaging characteristic parameters of the imaging devices and the standard imaging characteristic parameter. In addition, the image reception device includes a second communication unit, and an output unit. The second communication unit may wirelessly receive the frame image data from the image transmission devices. The output unit may output the frame image data.

According to a fourteenth aspect of the present invention, an imaging display system includes a plurality of imaging device, a plurality of image transmission devices, an image reception device, a display device, and a control device. The plurality of imaging devices image a subject and output frame image data. The plurality of image transmission devices are provided corresponding to each of the plurality of imaging devices, each of the image transmission devices wirelessly transmitting the frame image data output from the imaging devices. The image reception device wirelessly receives the wirelessly transmitted frame image data. The display device displays thereon images based on the frame image data wirelessly received by the image reception device. The control device controls wireless connection of the image transmission devices to the image reception device, wirelessly transmits a standard imaging characteristic parameter designated in advance, which is used as an index value when a processing parameter is adjusted, so as to reduce a difference in image qualities caused by imaging characteristics of each of the imaging devices to the image transmission devices, and transmits an adjustment target parameter of the quality of images to be displayed on the display device to the image reception device. In addition, each of the image transmission devices includes an input unit, a first image processing unit, a first communication unit, and a first adjustment unit. Imaging characteristic parameters of the imaging devices and the frame image data may be input to the input unit. The first image processing unit may perform image processing on the frame image data input to the input unit based on a first processing parameter. The first communication unit may wirelessly transmit the frame image data of an image that has been processed by the first image processing unit to the image reception device and wirelessly receive the standard imaging characteristic parameter from the control device. The first adjustment unit may adjust the first processing parameter based on the imaging characteristic parameters of the imaging devices and the standard imaging characteristic parameter. In addition, the image reception device includes a second communication unit, a second image processing unit, an output unit, and a second adjustment unit. The second communication unit may wirelessly receive the frame image data from the image transmission devices and wirelessly receive the adjustment target parameter from the control device. The second image processing unit may process the frame image data based on a second processing parameter. The output unit may output the frame image data processed by the second image processing unit. The adjustment unit may adjust the second processing parameter based on the adjustment target parameter.

BRIEF DESCRIPTION OF THE DRAWINGS

FIG. 15 is a referential table showing image quality adjustment target values according to the second embodiment of the present invention.

FIG. 16 is a referential table showing adjustment values of image processing according to the second embodiment of the present invention.

FIG. 20 is a referential table showing standard imaging characteristic values according to the third embodiment of the present invention.

FIG. 21 is a referential table showing adjustment values of imaging processing according to the third embodiment of the present invention.

FIG. 22 is a referential table showing image quality adjustment target values according to the third embodiment of the present invention.

FIG. 23 is a referential table showing display characteristics according to the third embodiment of the present invention.

FIG. 24 is a referential table showing adjustment values of imaging processing according to the third embodiment of the present invention.

DETAILED DESCRIPTION OF THE INVENTION

Hereinafter, embodiments of the present invention will be described with reference to the drawings.
(First Embodiment)

Figure 1:
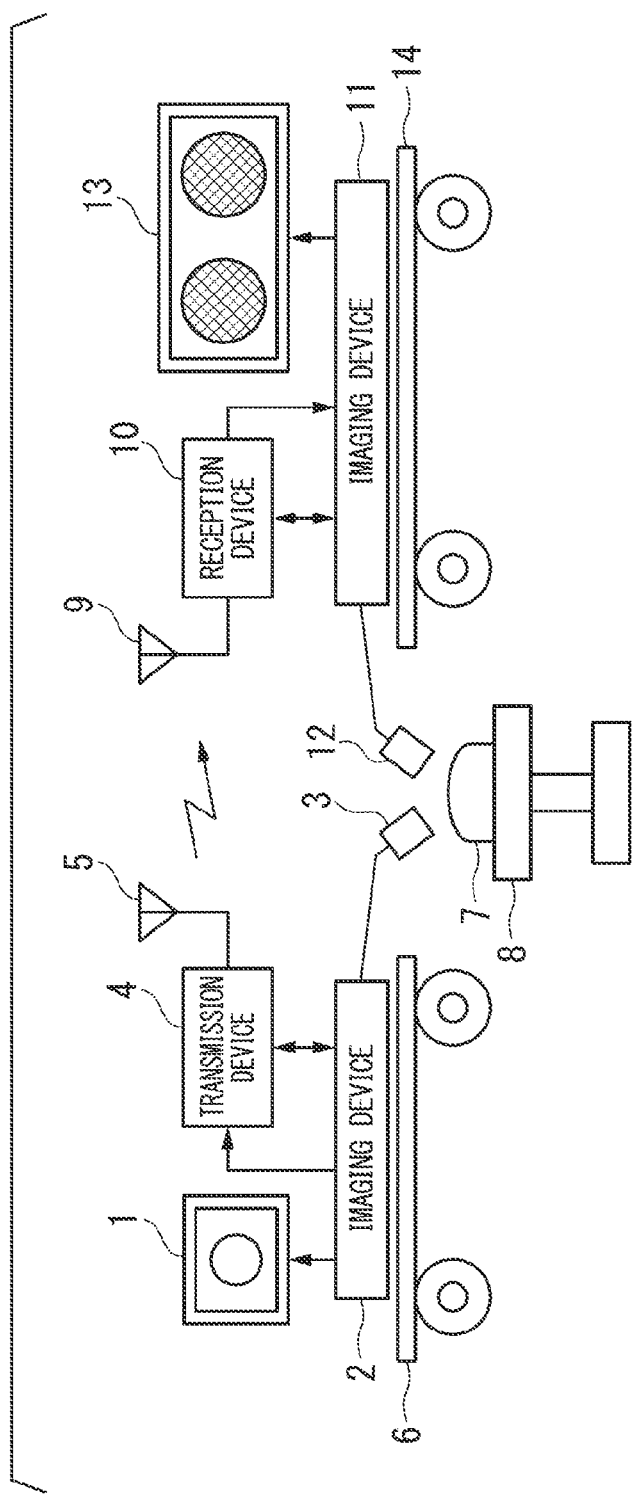
FIG. 1 is a block diagram showing the configuration of an imaging display system according to a first embodiment of the present invention.

First, a first embodiment of the present invention will be described. The present embodiment will be described with an example of an imaging display system that includes two medical imaging devices. In the present embodiment, a description will be provided with an example in which an embodiment of the present invention is applied to the imaging display system which is configured such that captured images obtained using a first medical imaging device are wirelessly transmitted to a second medical imaging device, and captured images obtained from both of the first and the second medical imaging devices are observed on a display monitor of the second medical imaging device. FIG. 1 shows the configuration of the imaging display system according to the present embodiment.

An imaging device 2 (a first imaging device), a monitor 1, and a transmission device 4 (an image transmission device) are mounted on a cart 6. The first imaging device 2 generates and outputs a first captured image using a camera head 3. The monitor 1 displays the first captured image and control information. The transmission device 4 wirelessly transmits the first captured image via an antenna 5. A reception device 10 (image reception device), an imaging device 11 (a second imaging device), and a monitor 13 (a display device) are mounted on a cart 14. The reception device 10 receives the first captured image from the transmission device 4 via an antenna 9 and outputs the image to the second imaging device 11. The second imaging device 11 generates a second captured image using a camera head 12, generates a display signal of a display state according to an instruction of a user based on the second captured image and the first captured image from the reception device 10, and outputs the signal to the monitor 13. The monitor 13 displays the first captured image and the second captured image based on the display signal from the second imaging device 11. The camera head 3 and the camera head 12 are disposed in appropriate positions in which an operation site of a patient 7 on a bed 8 is observed.

The first imaging device 2 images the operation site of the patient 7 who is a subject using the camera head 3, and thereby generates the first captured image. Meanwhile, the second imaging device 11 images the operation site of the patient 7 using the camera head 12, and thereby generates the second captured image. Data of the captured images is configured by image data of each frame (frame image data). In the description provided hereinbelow, the data of the captured images is configured by image data of one frame or a plurality of frames.

The first captured image which is generated by the first imaging device 2 is wirelessly transmitted to the reception device 10 by the transmission device 4 while being displayed on the monitor 1, and is displayed on the monitor 13 together with the second captured image which is generated by the second imaging device 11. Since imaging characteristics of the first imaging device 2 and the second imaging device 11 are different, an imaging processing circuit in the transmission device 4 converts the display image quality of the first captured image into the same display image quality as that of the second captured image using the imaging characteristics of the first imaging device 2 and the second imaging device 11, and then the transmission device 4 performs the wireless transmission of the first captured image.

When an operation is started, the transmission device 4 is notified of the imaging characteristic of the second imaging device 11. The transmission device 4 generates an adjustment value (processing parameter) to be used by the image processing circuit in the transmission device 4 in image processing using the notified imaging characteristic of the second imaging device 11 and the imaging characteristic of the first imaging device 2 being connected thereto. Accordingly, a difference in the image quality caused by the imaging characteristics of the imaging devices is reduced, and the first captured image and the second captured image are displayed on the monitor 13 with the same image quality. Details of the image processing will be described later.

Figure 2:
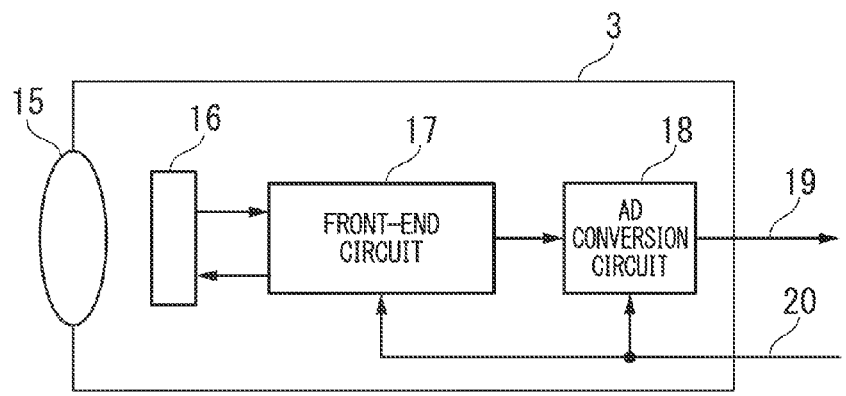
FIG. 2 is a block diagram showing the configuration of a camera head included in the imaging display system according to the first embodiment of the present invention.

A configuration of the camera head 3 will be described using FIG. 2. The camera head 3 includes an imaging optical system 15, an image sensor 16, a front-end circuit 17, and an AD conversion circuit 18. The imaging optical system 15 causes subject images to be formed on the image sensor 16. The image sensor 16 converts the subject images into imaging signals. The front-end circuit 17 processes the imaging signals output from the image sensor 16. The AD conversion circuit 18 converts the imaging signals processed in the front-end circuit 17 into digital data, and then outputs the data to the first imaging device 2 as a camera head output 19. The operations of the front-end circuit 17 and the AD conversion circuit 18 are controlled by a camera head control signal 20 from the first imaging device 2. Since the amount of the operation of the camera head 3 is common awareness, a further description thereof will be omitted here.

Figure 3:
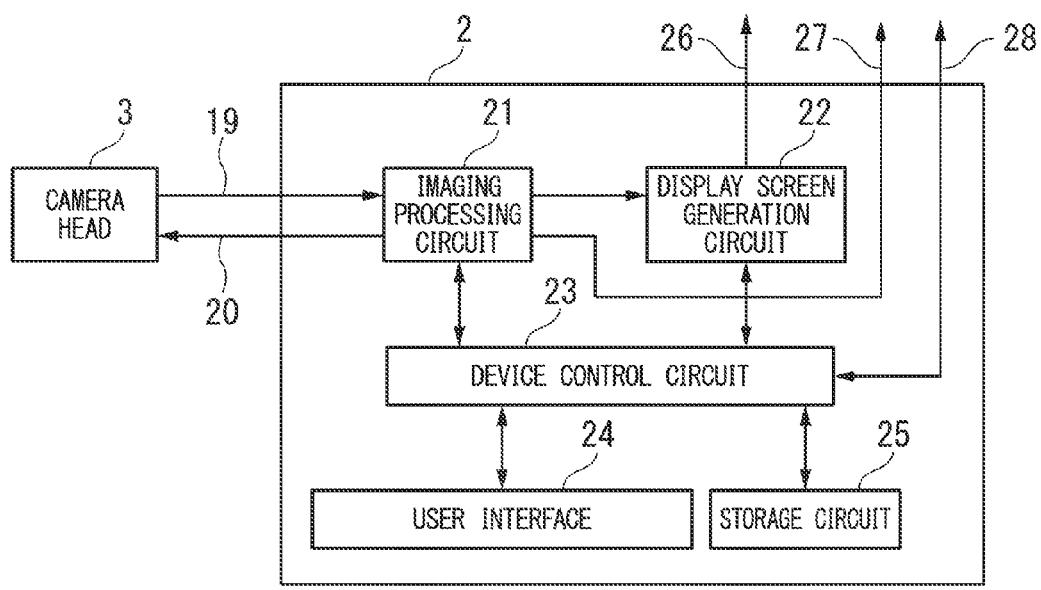
FIG. 3 is a block diagram showing the configuration of an imaging device included in the imaging display system according to the first embodiment of the present invention.

A configuration of the first imaging device 2 will be described using FIG. 3. The first imaging device 2 includes an imaging processing circuit 21, a display screen generation circuit 22, a device control circuit 23, a user interface 24, and a storage circuit 25. The imaging processing circuit 21 generates the first captured image by receiving the camera head output 19 from the camera head 3 and then performing an image quality adjustment process thereon and generates the camera head control signal 20 as well. The display screen generation circuit 22 generates a display signal 26 to display the first captured image on the monitor 1 based on the first captured image from the imaging processing circuit 21 and control information indicating an operation state of the first imaging device 2. The device control circuit 23 controls overall operations of the first imaging device 2. The user interface 24 delivers instructions of a user to the device control circuit 23. The storage circuit 25 stores the amount of the instructions of the user and various parameters, and the like indicating an imaging characteristic of the first imaging device 2. The first captured image from the imaging processing circuit 21 is output to the transmission device 4 as a captured image for transmission 27. In addition, a transmission device control signal 28 is output from the device control circuit 23. When an operation is started, an imaging characteristic value (an imaging characteristic parameter) indicating an imaging characteristic of the first imaging device 2 is output as the transmission device control signal 28.

Figure 4:
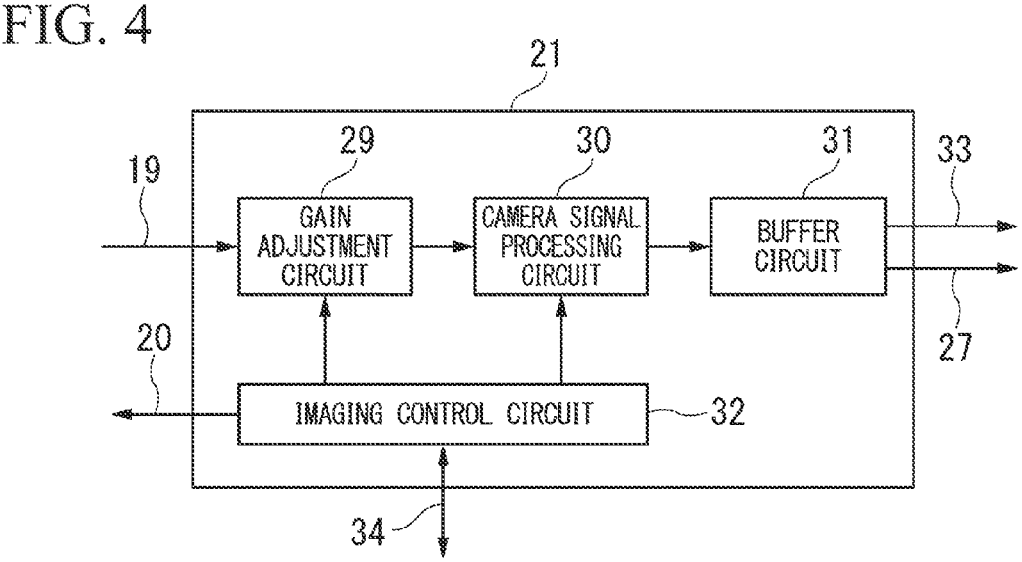
FIG. 4 is a block diagram showing the configuration of an imaging processing circuit in an imaging device included in the imaging display system according to the first embodiment of the present invention.

A configuration of the imaging processing circuit 21 in the first imaging device 2 will be described using FIG. 4. The imaging processing circuit 21 includes a gain adjustment circuit 29, a camera signal processing circuit 30, a buffer circuit 31, and an imaging control circuit 32. The gain adjustment circuit 29 performs a gain control process to the camera head output 19 from the camera head 3. The camera signal processing circuit 30 performs an image quality adjustment process to the signals processed in the gain adjustment circuit 29. The buffer circuit 31 performs output impedance conversion to the signals processed in the camera signal processing circuit 30 and then outputs the signals to the transmission device 4 as the captured image for transmission 27, and also outputs the signals to the display screen generation circuit 22 as a captured image for display 33. The imaging control circuit 32 controls the overall operations of the imaging processing circuit 21 in accordance with an imaging control signal 34 received from the device control circuit 23. In addition, the camera head control signal 20 is output from the imaging control circuit 32 in accordance with the imaging control signal 34 received from the device control circuit 23.

Figure 5:
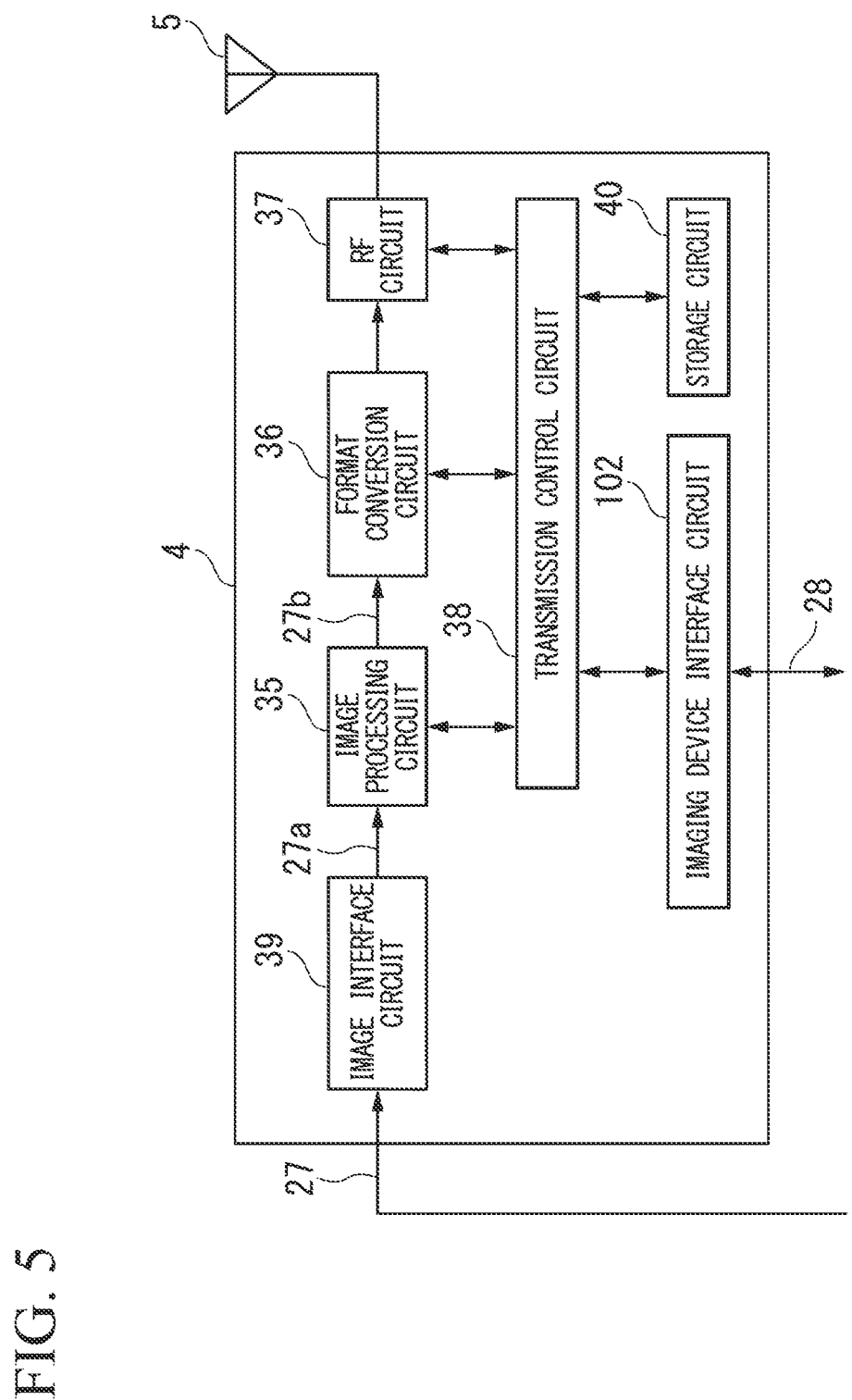
FIG. 5 is a block diagram showing the configuration of a transmission device included in the imaging display system according to the first embodiment of the present invention.

A configuration of the transmission device 4 will be described using FIG. 5. The transmission device 4 includes an image processing circuit 35 (an image processing unit or a first image processing unit), a format conversion unit 36, an RF circuit 37 (a communication unit), a transmission control circuit 38, an image interface circuit 39 (an input unit), an imaging device interface circuit 102 (an input unit), and a storage circuit 40. The captured image for transmission 27 received from the first imaging device 2 is input to the image interface circuit 39. The transmission device control signal 28 received from the first imaging device 2 is input to the imaging device interface circuit 102. The transmission device 4 performs image processing to the captured image for transmission 27 in accordance with an instruction indicated by the transmission device control signal 28, and then outputs a radio signal to the antenna 5.

The image processing circuit 35 performs image processing to a pre-processing image 27a output from the image interface circuit 39 using an adjustment value that is a parameter for the image processing. The format conversion circuit 36 converts a post-processing image 27b output from the image processing circuit 35 so as to be in a predetermined communication format. The RF circuit 37 turns the first captured image, which is output from the format conversion circuit 36 and is in a converted format, into radio data, and then transmits the image to the reception device 10 via the antenna 5. In addition, data which is obtained by turning an imaging characteristic value of the second imaging device 11 into radio data is transmitted from the reception device 10 when an operation is started, and the RF circuit 37 receives the data via the antenna 5, and then delivers the imaging characteristic value of the second imaging device 11 to the transmission control circuit 38. The imaging characteristic value of the second imaging device 11 is delivered to the imaging processing circuit 35 by the transmission control circuit 38. Details of the image processing performed by the image processing circuit 35 will be described later using FIG. 8.

The transmission device control signal 28 received from the device control circuit 23 of the first imaging device 2 is input to the imaging device interface circuit 102, and the imaging characteristic value of the first imaging device 2 is delivered to the image processing circuit 35 via the transmission control circuit 38. The transmission control circuit 38 controls the overall operations of the transmission device 4. The storage circuit 40 stores various parameters, and the like.

Figure 6:
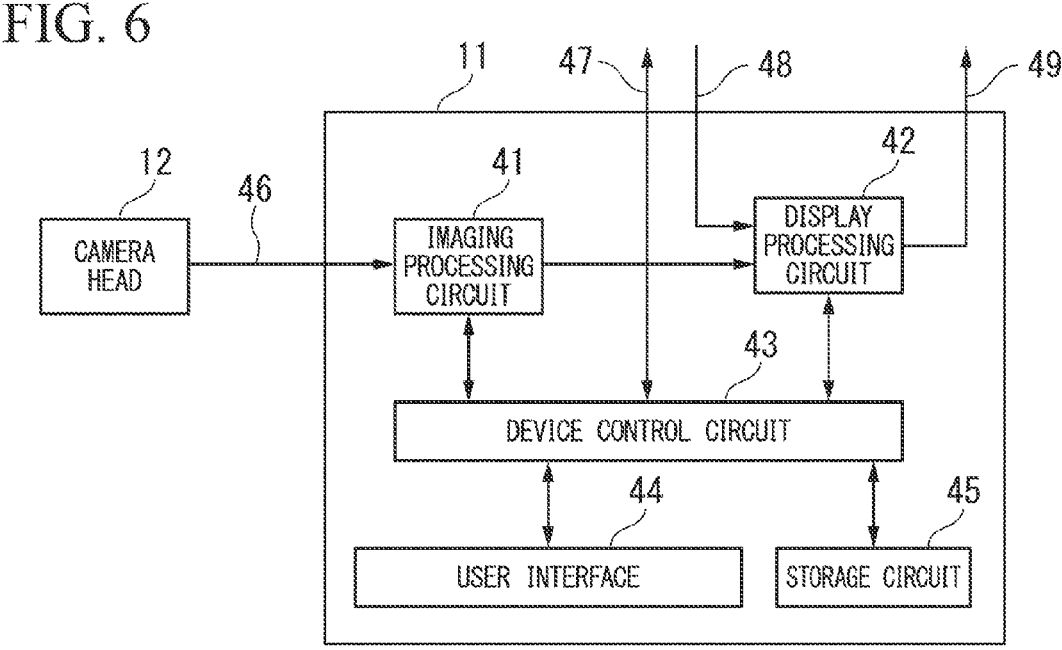
FIG. 6 is a block diagram showing the configuration of another imaging device included in the imaging display system according to the first embodiment of the present invention.

A configuration of the second imaging device 11 will be described using FIG. 6. The second imaging device 11 includes an imaging processing circuit 41, a display processing circuit 42, a device control circuit 43, a user interface 44, and a storage circuit 45. The configuration of the second imaging device 11 is basically the same as that of the first imaging device 2, but has a difference in a configuration of the display processing circuit 42 that generates a monitor display signal 49 to be output to the monitor 13 using the second captured image received from the camera head 12 and the first captured image received from the reception device 10.

The display processing circuit 42 is input with the second captured image received from the imaging processing circuit 41 and a received image signal 48 (corresponding to the first captured image) received from the reception device 10, and thereby generates the monitor display signal 49 to be displayed on the monitor 13 received from the second captured image and the received image signal 48. The monitor 13 is capable of displaying only the first captured image, only the second captured image, or a multi-screen of the first captured image and the second captured image. The device control circuit 43 gives instructions to the display processing circuit 42 in accordance with instructions of a user input to the user interface 44. In addition, when an operation is started, the device control circuit 43 outputs the imaging characteristic value of the second imaging device 11 to the reception device 10 as a reception device control signal 47.

Figure 7:
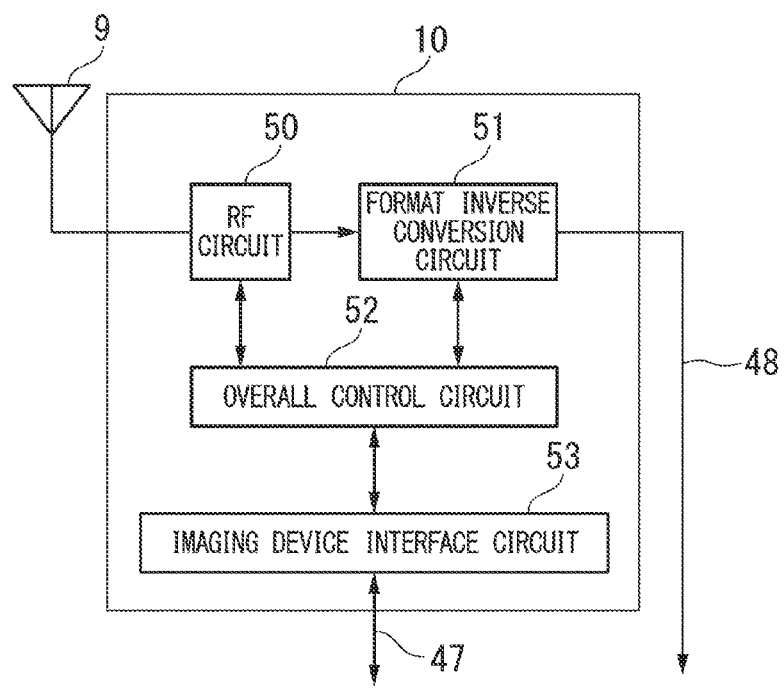
FIG. 7 is a block diagram showing the configuration of a reception device included in the imaging display system according to the first embodiment of the present invention.

A configuration of the reception device 10 will be described using FIG. 7. The reception device 10 includes an RF circuit 50 (a second communication unit), a format inverse conversion circuit 51 (an output unit), an overall-control circuit 52, and an imaging device interface circuit 53. The RF circuit 50 receives radio data that is wirelessly transmitted from the transmission device 4 via the antenna 9, and performs a high-frequency process. The format inverse conversion circuit 51 inversely converts the format of the radio data that the RF circuit 50 receives so as to return the data to the first captured image, and then outputs the image to the second imaging device 11 as the received image signal 48. The overall-control circuit 52 controls the overall operations of the reception device 10.

The imaging device interface circuit 53 is connected to the second imaging device 11 by the reception device control signal 47. When an operation is started, the imaging characteristic value of the imaging device 11 is input to the imaging device interface circuit 53 by the reception device control signal 47, and delivered to the overall control circuit 52 via the imaging device interface circuit 53. The overall control circuit 52 outputs the imaging characteristic value of the second imaging device 11 to the RF circuit 50. The RF circuit 50 transmits data obtained by turning the imaging characteristic value of the second imaging device 11 into radio data to the transmission device 4 via the antenna 9.

A configuration of the image processing circuit 35 in the transmission device 4 will be described using FIG. 8. The image processing circuit 35 includes a color balance adjustment circuit 54, a gamma adjustment circuit 55, a frequency characteristic adjustment circuit 56, and an adjustment value control circuit 57 (an adjustment unit). The captured image for transmission 27 received from the first imaging device 2 includes Y (luminance), U (color difference-Cb), and V (color difference-Cr), and is input to the color balance adjustment circuit 54 as the pre-processing image 27a. The color balance adjustment circuit 54 adjusts a color gain and a hue angle of the pre-processing image 27a. The gamma adjustment circuit 55 performs gamma adjustment to the image processed in the color balance adjustment circuit 54. The frequency characteristic adjustment circuit 56 performs frequency adjustment on the image processed in the gamma adjustment circuit 55, and outputs the post-processing image 27b. The adjustment value control circuit 57 controls the overall operations of the image processing circuit 35 in accordance with an instruction received from the transmission control circuit 38. Details of the adjustment of a color gain and a hue, gamma adjustment, and frequency adjustment included in the image quality adjustment performed by the image processing circuit 35 will be described later.

Figures 8, 9:
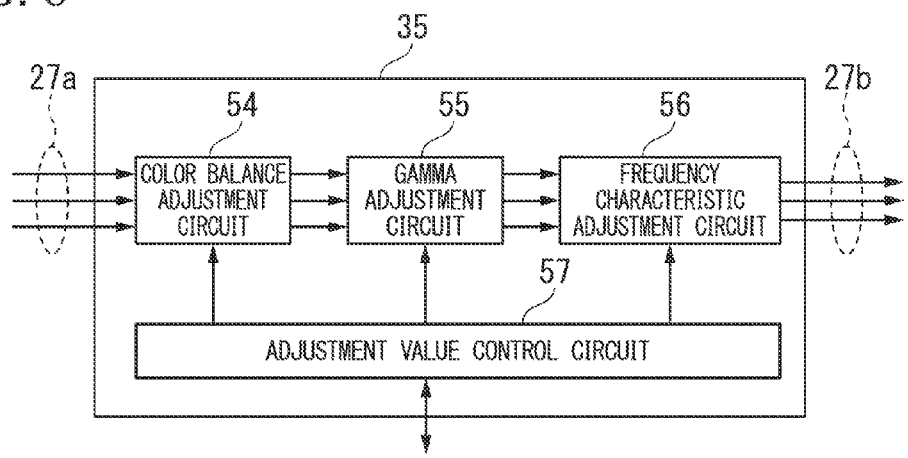
FIG. 8 is a block diagram showing the configuration of an imaging processing circuit in the transmission device included in the imaging display system according to the first embodiment of the present invention.
FIG. 9 is a referential table showing imaging characteristic values according to the first embodiment of the present invention.

FIG. 9 shows an example of imaging characteristic values used in the image quality adjustment performed by the image processing circuit 35 of the transmission device 4. The imaging characteristic values indicate imaging characteristics of each of the imaging devices. As shown in FIG. 9, the imaging characteristic values include color gains which are saturation characteristic values of a captured image, hue angles (0 to ±180 degrees) which are hue (HUE) characteristic values, gamma which is a gamma characteristic value of the captured image, and frequency characteristics which are frequency characteristic values of the captured image. Note that the frequency characteristics are displayed after normalizing a sampling frequency to be 1. The frequency characteristics are defined by gains in each frequency of 0, 0.1, 0.2, 0.3, 0.4, and 0.5 in both horizontal (H) and vertical (V) directions.

The image quality adjustment is performed according to the imaging characteristic values. When the imaging characteristics of the first imaging device 2 are characteristics of ID_a shown in FIG. 9 and the characteristics of the second imaging device 11 are characteristics of ID_b, for example, in order to transmit the first captured image that has been captured with a color gain of 1.1 so as to have the same image quality as that of the second captured image captured with a color gain of 0.8, it is necessary to adjust the color gain by 0.73 (=0.8/1.1) times. Likewise, it is necessary to adjust the hue angle by −20 degrees (=−10-10).

In the present embodiment, the transmission device 4 is notified of the imaging characteristic values of the second imaging device 11 via the reception device 10 immediately after an operation is started as described above. On the other hand, the transmission device 4 is notified of the imaging characteristic values of the first imaging device 2 by the first imaging device 2. In the image processing circuit 35 of the transmission device 4, the adjustment value control circuit 57 decides adjustment values of the color balance adjustment circuit 54, the gamma adjustment circuit 55, and the frequency characteristic adjustment circuit 56 based on the imaging characteristic values of the second imaging device 11 and the imaging characteristic values of the first imaging device 2 notified of by the transmission control circuit 38, and sets adjustment values to each of the circuits. The adjustment of gamma and frequency characteristics will be described using FIG. 10 and FIG. 11.

Figure 10:
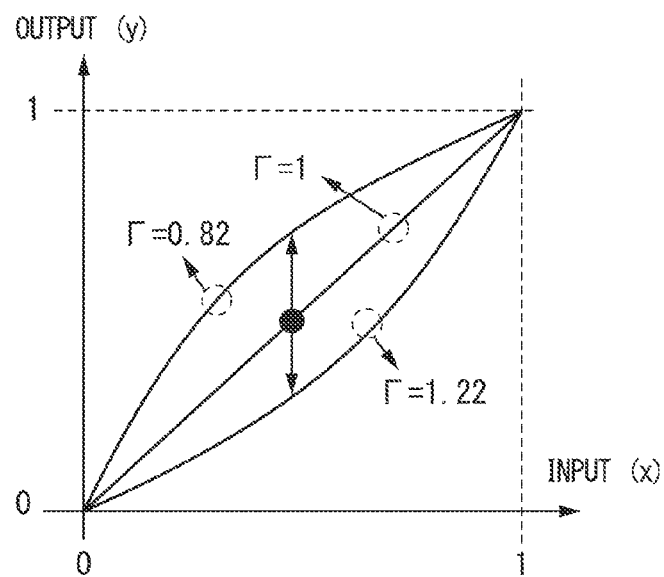
FIG. 10 is a referential graph showing gamma correction according to the first embodiment of the present invention.

FIG. 10 shows an example of gamma correction. For a general display monitor, a gamma value of a device is set to be 2.2 or 1.8. For this reason, for such a general display monitor, an imaging device performs inverse correction (1/γ correction) in which the gamma of the display monitor is offset in a state in which the imaging device is connected to the display monitor so as to set gamma=1. For this reason, a gamma characteristic value of an imaging device is set to be gamma=0.45 (=1/2.2) or 0.55 (=1/1.8). When a gamma characteristic value of the imaging device 2 is 0.45 and a gamma characteristic value of the second imaging device 11 is 0.55, in gamma adjustment performed by the gamma adjustment circuit 55, gamma correction is performed on the first captured image so as to set gamma=1.22 (=0.55/0.45). In addition, when a gamma characteristic value of the first imaging device 2 is 0.55 and a gamma characteristic value of the second imaging device 11 is 0.45, the gamma adjustment circuit 55 performs correction so as to set gamma=0.82 (=0.45/0.55). When the first imaging device 2 and the second imaging device 11 have the same gamma characteristic value, it is set to be gamma=1 (no adjustment). In the gamma adjustment circuit 55, a table having the input and output relationship (F=0.82, 1, and 1.22) shown in FIG. 10 is prepared, and the table is used in a switching manner according to an instruction received from the adjustment value control circuit 57.

Figure 11:
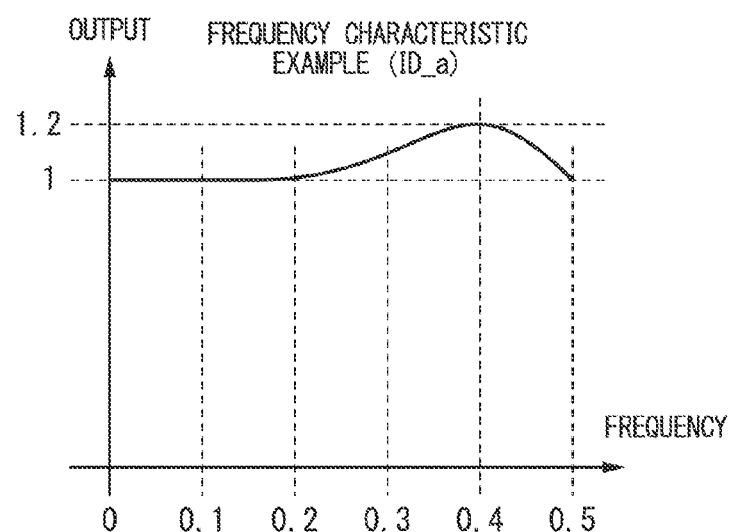
FIG. 11 is a referential graph showing a frequency characteristic according to the first embodiment of the present invention.

FIG. 11 shows a frequency characteristic of the first imaging device 2. As shown in FIG. 9, the frequency characteristic of the first imaging device 2 is normalized with the sampling frequency of 1. As shown in FIG. 11, with regard to the frequency characteristic of the first imaging device 2, the gains are 1.0, 1.0, 1.0, 1.1, 1.2, and 1.0 each in the frequencies of 0, 0.1, 0.2, 0.3, 0.4, and 0.5. With regard to the frequency characteristic of the second imaging device 11, the gains are 1.0, 1.0, 1.0, 1.2, 1.3, and 1.0 each in the frequencies of 0, 0.1, 0.2, 0.3, 0.4, and 0.5. In order to match each gain of the frequencies of the first captured image and each gain of the frequencies of the second captured image, frequency adjustment values are 1.0, 1.0, 1.0, 1.1, 1.1, and 1.0 obtained by dividing each gain of the frequencies of the second captured image by each gain of the frequencies of the first captured image. The frequency characteristic adjustment circuit 56 has a digital filter circuit therein for realizing the frequency adjustment described above, and performs the frequency adjustment by adjusting a filter coefficient.

Using the method described above, the transmission device 4 converts the quality of the first captured image so as to be the same quality as the second captured image, and performs wireless transmission. Accordingly, the difference in the image quality caused by the imaging characteristics of the imaging devices is cancelled, and accordingly, the first captured image and the second captured image are displayed on the monitor 13 with the same image quality.

As described above, according to the present embodiment, when the adjustment values are adjusted so that the difference in the image quality caused by the imaging characteristics of the imaging devices is reduced, by adjusting the adjustment values of the image processing circuit 35 based on the imaging characteristic value of the first imaging device 2 and the imaging characteristic value of the second imaging device 11, the difference in the quality of the images displayed on the monitor 13 can be reduced regardless of an imaging device in use.

(Second Embodiment)

Figure 12:
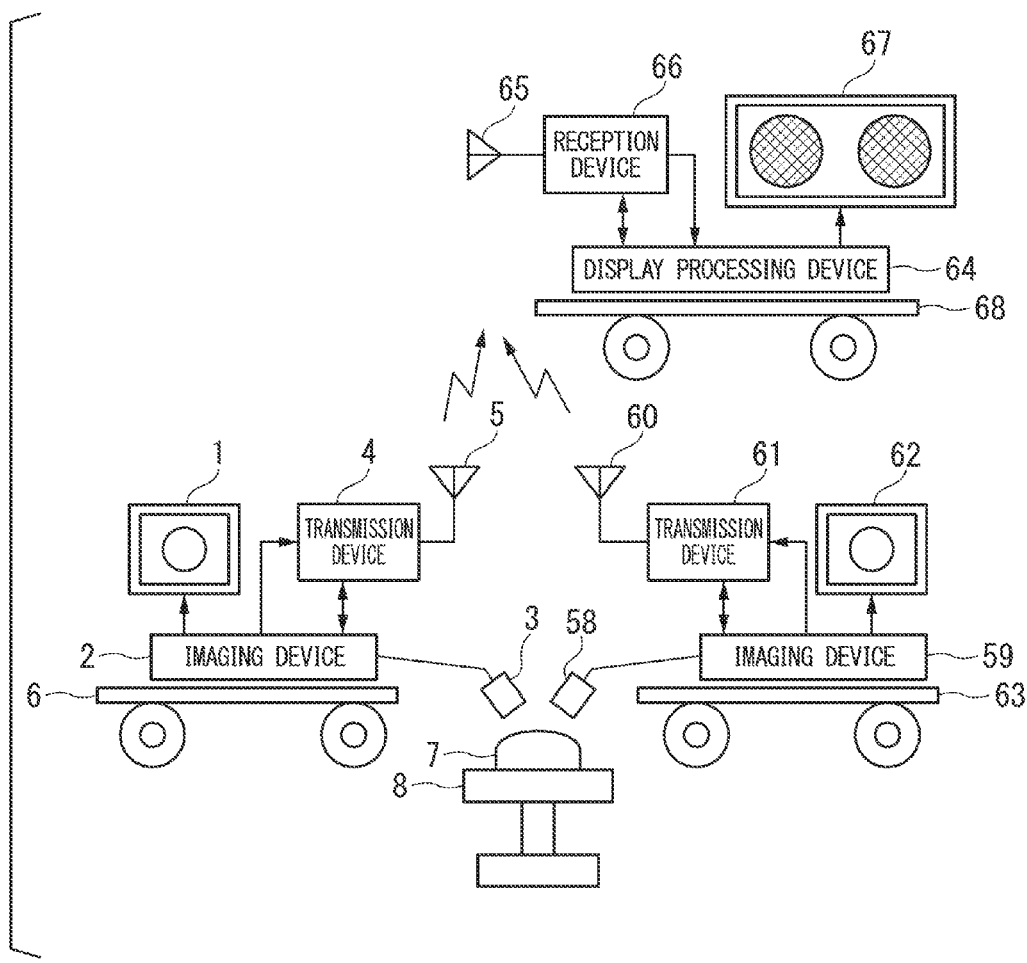
FIG. 12 is a block diagram representing a configuration of an imaging display system according to a second embodiment of the present invention.

Next, a second embodiment of the present invention will be described. The present embodiment will be described exemplifying an imaging display system constituted by two medical imaging devices and one image display device. In the present embodiment, description will be provided with an example in which an embodiment of the present invention is applied to the imaging display system configured such that captured images obtained by the two medical imaging devices are wirelessly transmitted to the image display device, and the captured images of both devices can be observed using the image display device. FIG. 12 shows the configuration of the imaging display system according to the present embodiment.

In the cart 6, the camera head 3, the first imaging device 2, the monitor 1, and the transmission device 4 having the same constitution as in the first embodiment are mounted. In the cart 63 having the same configuration as the cart 6, a camera head 58, an imaging device 59, a monitor 62, and a transmission device 61 are mounted. The camera head 3 and the camera head 58 are disposed in appropriate positions in which an operation site of the patient 7 on the bed 8 is observed, as in the first embodiment.

In the cart 68, a reception device 66, a display processing device 64, and a monitor 67 are mounted. The reception device 66 receives a first captured image from the transmission device 4 and a second captured image from the transmission device 61 via the antenna 65. The display processing device 64 accepts the first captured image and the second captured image from the reception device 66, generates display signals based on the captured images, and outputs the signals to the monitor 67. The monitor 67 displays the first captured image and the second captured image thereon based on the display signal received from the display processing device 64. The configuration of the reception device 66 is the same as that of the reception device 10 described using FIG. 7.

The first captured image which is generated in the first imaging device 2 is displayed on the monitor 1, and at the same time wirelessly transmitted to the reception device 66 by the transmission device 4. The second captured image which is generated in the imaging device 59 is also displayed on the monitor 62, and at the same time wirelessly transmitted to the reception device 66 by the transmission device 61. The transmission device 66 receives the first captured image and the second captured image, and outputs the images to the display processing device 64. The display processing device 64 generates display signals from the first captured image and the second captured image, and outputs the signals to the monitor 67. The monitor 67 displays the first captured image and the second captured image based on the display signals.

By adjusting adjustment values of image processing circuits in the transmission device 4 and the transmission device 61, the quality of the first captured image and the second captured image displayed on the monitor 67 is adjusted to be predetermined image quality. In the adjustment of the adjustment values of the image processing circuits in the transmission device 4 and the transmission device 61, an image quality adjustment target value indicating the quality of an image displayed on the monitor 67 is used. This image quality adjustment target value is a target value of a parameter corresponding to the quality of a captured image that a user desires. In addition, the image quality adjustment target value is based on a characteristic generated from a combination of imaging characteristics of the first imaging devices 2 and 59 and characteristics of image quality adjustment (image processing) performed by the image processing circuits of the transmission devices 4 and 61. Although the image quality adjustment target value is based on the imaging characteristics of the imaging devices and the characteristics of the image quality adjustment by the image processing circuits as described above, the characteristics are not individually designated. Absolutely, the image quality adjustment target value indicates a characteristic of image quality that is finally obtained by reflecting the characteristics of the imaging devices and the characteristics of the image quality adjustment of the image processing circuits.

The image quality adjustment target value is retained in the display processing device 64. The image quality adjustment target value is wirelessly transmitted to the transmission device 4 and the transmission device 61 via the reception device 66 when an operation is started. The wireless transmission of the image quality adjustment target value to the transmission device 4 and the transmission device 61 from the reception device 66 is the same as the wireless transmission of the imaging characteristic value of the second imaging device 11 from the reception device 10 to the transmission device 4 in the first embodiment. In addition, the transmission device 4 is notified of the imaging characteristic of the second imaging device 11 when an operation is started as in the first embodiment. In addition, the transmission device 61 is notified of the imaging characteristic of the imaging device 59.

The transmission device 4 and the transmission device 61 decide adjustment values of the image processing circuits from the imaging characteristics of the first imaging device 2 and the imaging device 59 respectively connected to the transmission devices and the shared image quality adjustment target value. In this case, the adjustment values of each of the image processing circuits are decided so that parameters of image quality obtained in such a way that the image processing circuits of the transmission device 4 and the transmission device 61 process the captured images coincide with a parameter of image quality indicated by the shared image quality adjustment target value. Accordingly, the difference in the image quality caused by the imaging characteristics of the imaging devices is cancelled, and the first captured image and the second captured image are displayed on the monitor 67 with the same image quality indicated by the image quality adjustment target value. The image processing described above will be described later in more detail.

A configuration of the display processing device 64 will be described using FIG. 13. The display processing device 64 includes a frame memory circuit 69, a display screen generation circuit 70, a device control circuit 71, a user interface 72, and a storage circuit 73. The frame memory circuit 69 temporarily stores a received image signal 75 output from the reception device 66. The first captured image and the second captured image corresponding to the received image signal written on the frame memory circuit 69 are read at a desired timing and output to the display screen generation circuit 70. The display screen generation circuit 70 generates a display signal 76 by organizing the first captured image and the second captured image read from the frame memory circuit 69 and various kinds of control information from the device control circuit 71.

The device control circuit 71 controls the overall operations of the display processing device 64. In addition, the device control circuit 71 generates the image quality adjustment target value and retains the value in the storage circuit 73, and outputs the image quality adjustment target value to the reception device 66 as a reception device control signal 74 when the image processing circuits of the transmission device 4 and the transmission device 61 perform image quality adjustment. The user interface 72 delivers a user instruction to the device control circuit 71. The storage circuit 73 stores the content of the user instruction, the image quality adjustment target value, and the like.

Next, image quality adjustment performed by the image processing circuits of the transmission device 4 and the transmission device 61 will be described using FIGS. 14 to 16. The image quality adjustment is a process performed by the image processing circuits of the transmission devices on the captured images using the imaging characteristics of the image devices in connection based on the image quality adjustment target value from the display processing device 64. With the image quality adjustment, the qualities of the first captured image and the second captured image displayed on the monitor 67 come to be the same as indicated by the image quality adjustment target value.

Figures 13, 14:
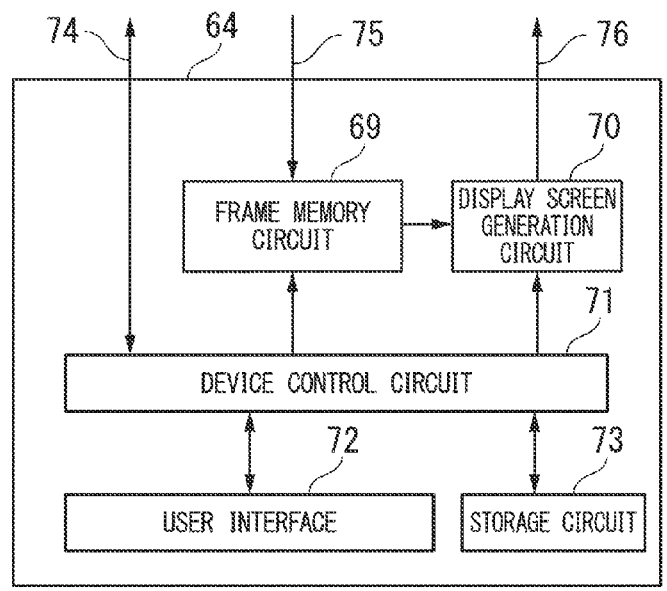
FIG. 13 is a block diagram representing a configuration of a display processing device included in the imaging display system according to the second embodiment of the present invention.
FIG. 14 is a referential table showing imaging characteristic values according to the second embodiment of the present invention.

FIG. 14 shows imaging characteristic values of the first imaging device 2 and the imaging device 59. In FIG. 14, information of ID_a is imaging characteristic values of the first imaging device 2, and information of ID_b is imaging characteristic values of the imaging device 59.

FIG. 15 shows an example of image quality adjustment target values. The image quality adjustment target values of the present embodiment are defined corresponding to preferred image quality of each user who observes the monitor 67. The image quality adjustment target values include a color gain that is a saturation characteristic value of an imaging device, a hue angle (0 to ±180 degrees) that is a hue (HUE) characteristic value, gamma that is a gamma characteristic value of an imaging device, and a frequency characteristic that is a frequency characteristic value of an imaging device. In FIG. 15, as an example, image quality adjustment target values corresponding to preferred image quality of a user whose user ID is MD1 are defined.

FIG. 16 shows adjustment values (processing parameters) of image processing in the image processing circuits of the transmission device 4 and the transmission device 61 when the imaging characteristic values shown in FIG. 14 and the image quality adjustment target values shown in FIG. 15 are used.

First, a generation method of the image quality adjustment target values will be described. The procedure of generating the image quality adjustment target values will be described in detail exemplifying a case of using the first imaging device 2. The device control circuit 71 of the display processing device 64 generates the image quality adjustment target values and retains them in the storage circuit 73. To be specific, in the state in which a user whose user ID is MD1 observes the first captured image received from the first imaging device 2 on the monitor 67, the user operates the user interface 72 of the display processing device 64 to adjust the quality of the first captured image displayed on the monitor 67 to his or her preferred image quality.

In this case, the content of the operation of the user is transferred from the display processing device 64 to the reception device 66, then wirelessly transmitted from the reception device 66 to the transmission device 4, and delivered to the image processing circuit 35 of the transmission device 4. In the image processing circuit 35, the adjustment value control circuit 57 updates adjustment values of the color balance adjustment circuit 54, the gamma adjustment circuit 55, and the frequency characteristic adjustment circuit 56 based on the content of the operation of the user. As a result, the quality of the first captured image displayed on the monitor 67 is adjusted.

The image quality adjustment target values are generated using the adjustment values of the image processing circuit 35 at the time when the quality of the first captured image displayed on the monitor 67 becomes the preferred image quality of the user. For the field of a transmission device TX_a of FIG. 16, examples of adjustment values decided in accordance with the procedure of generating the image quality adjustment target values described above are shown.

When the adjustment values of the image processing circuit 35 are the values shown in FIG. 16, the imaging characteristic values of the first imaging device 2 are the values shown in FIG. 14, and thus the image quality adjustment target values are the values shown in FIG. 15. For example, with regard to a color gain, the adjustment value is 0.82, and the imaging characteristic value is 1.1, and thus the image quality adjustment target value is 0.9 (=0.82×1.1). Likewise, with regard to a hue angle, the adjustment value is −5 degrees and the imaging characteristic value is +10 degrees, and thus the image quality adjustment target value is +5 degrees. With regard to gamma, the adjustment value is 1.11 and the imaging characteristic value is 0.45, and thus the image quality adjustment target value is 0.5 (=1.11× 0.45). With regard to a frequency characteristic, the adjustment values are 1, 1, 1, 1, 1, and 1.1 and the imaging characteristic values are 1, 1, 1, 1.1, 1.2, and 1, and thus the image quality adjustment target values are 1, 1, 1, 1, 1.2, and 1.1.

During the generation of the image quality adjustment target values, since the adjustment values of the image processing circuit 35 are decided by the operation from the display processing device 64, the storage circuit 73 of the display processing device 64 also retains the adjustment values of the image processing circuit 35. The device control circuit 71 of the display processing device 64 generates the image quality adjustment target values through the procedure described above.

Next, setting of the adjustment values of the image processing circuits of the transmission devices during an operation will be described. When the image quality adjustment target values are the values shown in FIG. 15, the adjustment values of the image processing circuits of the transmission device 4 and the transmission device 61 are the values shown in FIG. 16. Herein, an example of setting the adjustment values of the image processing circuit of the transmission device 61 will be described using the values shown in FIGS. 14 to 16.

The adjustment values (of FIG. 16) of the image processing circuit of the transmission device 61 are decided from the image quality adjustment target values (FIG. 15) and the imaging characteristic values of the imaging device 59 (FIG. 14). To be specific, with regard to a color gain, the image quality adjustment target value is 0.9 and the imaging characteristic value is 1.2, and thus the adjustment value is 0.75 (=0.9/1.2). Likewise, with regard to a hue angle, the image quality adjustment target value is +5 degrees and the imaging characteristic value is +20 degrees, and thus the adjustment value is −15 degrees. With regard to gamma, the image quality adjustment target value is 0.5 and the imaging characteristic value is 0.56, and thus the adjustment value is 0.89 (=0.5/0.56). With regard to a frequency characteristic, the image quality adjustment target values are 1, 1, 1, 1, 1.2, and 1.1 and the imaging characteristic values are 1, 1, 1, 1.2, 1.2, and 1, and thus the adjustment values are 1, 1, 1, 0.83, 1, and 1.1.

The adjustment value control circuit in the image processing circuit of the transmission device 61 decides the adjustment values of the color gain, hue angle, gamma, and frequency characteristic based on the image quality adjustment target values and the imaging characteristic values of the imaging device 59, and sets the adjustment values in each circuit. For the transmission device 4, adjustment values are decided in the same procedure. With the decision of the adjustment values as described above, the difference in image qualities caused by the imaging characteristics of the imaging devices is cancelled, and the qualities of the first captured image and the second captured image displayed on the monitor 67 have the values indicated by the image quality adjustment target values.

As described above, according to the present embodiment, when the adjustment values are adjusted so that the difference in the image qualities caused by the imaging characteristics of the imaging devices is reduced, the adjustment values of the image processing circuit 35 of the transmission device 4 are adjusted based on the imaging characteristic values and the image quality adjustment target values of the first imaging device 2, and the adjustment values of the image processing circuit of the transmission device 61 are adjusted based on the imaging characteristic values and the image quality adjustment target values of the imaging device 59. Accordingly, it is possible to reduce the difference in the qualities of images displayed on the monitor 67 regardless of imaging devices in use.

(Third Embodiment)

Figure 17:
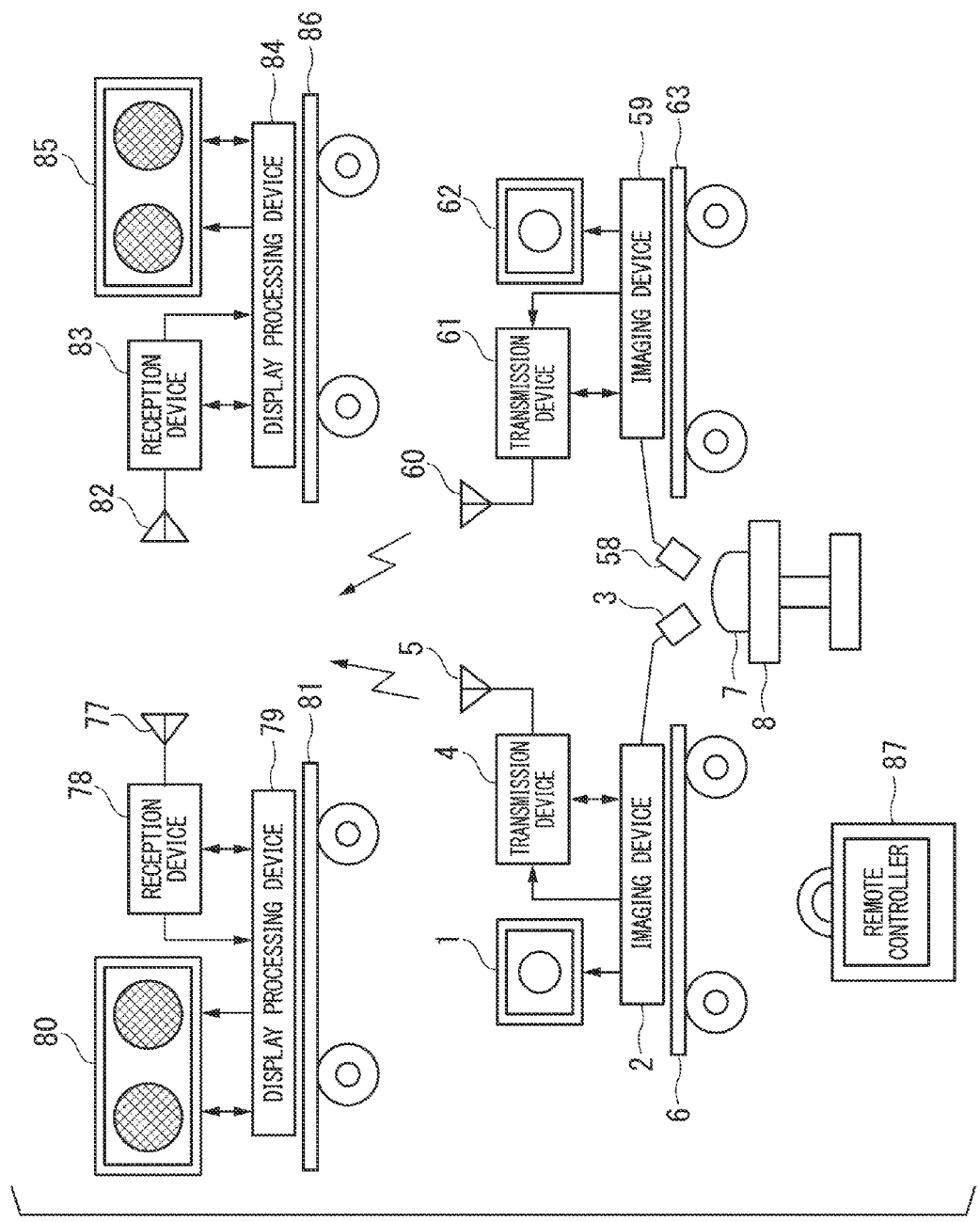
FIG. 17 is a block diagram showing the configuration of an imaging display system according to a third embodiment of the present invention.

Next, a third embodiment of the present invention will be described. In the present embodiment, an example of an imaging display system configured by two medical imaging devices, two image display devices, and a connection setting device (a remote controller) will be described. A case in which an embodiment of the present invention is applied to the imaging display system configured such that, according to setting of wireless connection decided by the connection setting device, captured images obtained by the two medical imaging devices are wirelessly transmitted to the two image display devices, and both captured images can be observed by the two image display device will be exemplified. FIG. 17 illustrates the configuration of the imaging display system according to the present embodiment.

The configurations of the cart 6 and the cart 63 are the same as those in the second embodiment. In the cart 81, a reception device 78, a display processing device 79, and a monitor 80 are mounted. The reception device 78 receives a first captured image from the transmission device 4 and a second captured image from the transmission device 61 via the antenna 77. The display processing device 79 accepts the first captured image and the second captured image from the reception device 78, and generates display signals based on the captured images and outputs them to the monitor 80. The monitor 80 displays the first captured image and the second captured image based on the display signals received from the display processing device 79.

The configuration of the cart 86 is the same as that of the cart 81. In the cart 86, the reception device 83, the display processing device 84, and the monitor 85 are mounted. The reception device 83 receives the first captured image from the transmission device 4 and the second captured image from the transmission device 61 via the antenna 82. The configurations of the cart 81 and the cart 86 are substantially the same as that of the cart 68 of the second embodiment, but the reception device 78 and the reception device 83 each has an image quality adjustment function, which is different from the reception device 66 of the second embodiment. In addition, the present embodiment is configured such that there are two monitors on which the images are displayed, and the remote controller 87 (the control device) controls wireless connection of each transmission device and each reception device, and thereby a combination of a transmission device and a reception device to be wirelessly connected is capable of being decided freely. Accordingly, captured images displayed on each monitor using the remote controller 87 is capable of being decided freely.

The first captured image which is generated in the first imaging device 2 is displayed on the monitor 1, and at the same time wirelessly transmitted to the reception device 78 and the reception device 83 by the transmission device 4. The second captured image which is generated in the imaging device 59 is also displayed on the monitor 62, and at the same time wirelessly transmitted to the reception device 78 and the reception device 83 by the transmission device 61. The reception device 78 receives the first captured image and the second captured image, and outputs the images to the display processing device 79. The reception device 83 receives the first captured image and the second captured image, and outputs the images to the display processing device 84.

The display processing device 79 generates display signals from the first captured image and the second captured image, and outputs the signals to the monitor 80. The monitor 80 displays the first captured image and the second captured image based on the display signals. The display processing device 84 generates display signals from the first captured image and the second captured image and outputs the signals to the monitor 85. The monitor 85 displays the first captured image and the second captured image based on the display signals.

By adjusting adjustment values of image processing circuits in the transmission device 4 and the transmission device 61 and adjustment values of an image processing circuit in the reception device 78, the qualities of the first captured image and the second captured image displayed on the monitor 80 are adjusted so as to be predetermined image quality set for each user of the monitor. In addition, by adjusting the adjustment values of the image processing circuits in the transmission device 4 and the transmission device 61 and adjustment values of an image processing circuit in the reception device 83, the qualities of the first captured image and the second captured image displayed on the monitor 85 are adjusted so as to be predetermined image quality set for each user of the monitor. In the present embodiment, an example in which a displayed image quality of the monitor 80 and a displayed image quality of the monitor 85 are adjusted so as to be different will be described.

Image quality adjustment target values indicating the quality of images displayed on each monitor are retained in the remote controller 87. The image quality adjustment target values are wirelessly transmitted to the reception device 78 and the reception device 83 when connection is set by the remote controller 87. In addition, in order to make the qualities of the captured images transmitted from the transmission device 4 and the transmission device 61 uniform, standard imaging characteristic values (standard imaging characteristic parameters) which are a standard imaging characteristic designated in advance are used. The standard imaging characteristic values are also retained in the remote controller 87, and wirelessly transmitted to the transmission device 4, the transmission device 61, the reception device 78, and the reception device 83 during connection setting by the remote controller 87.

The quality of the first captured image of the present embodiment is adjusted to an image quality corresponding to a standard imaging characteristic by the image processing circuit 35 in the transmission device 4. In addition, the quality of the second captured image of the present embodiment is adjusted to an image quality corresponding to a standard imaging characteristic by the image processing circuit in the transmission device 61. In this manner, the first captured image and the second captured image are wirelessly transmitted with the same image quality, and are adjusted with the image qualities to be image qualities corresponding to image quality adjustment target values designed for each monitor connected in the reception device 78 and the reception device 83 thereto. Details of the image processing described above will be described later.

Figure 18:
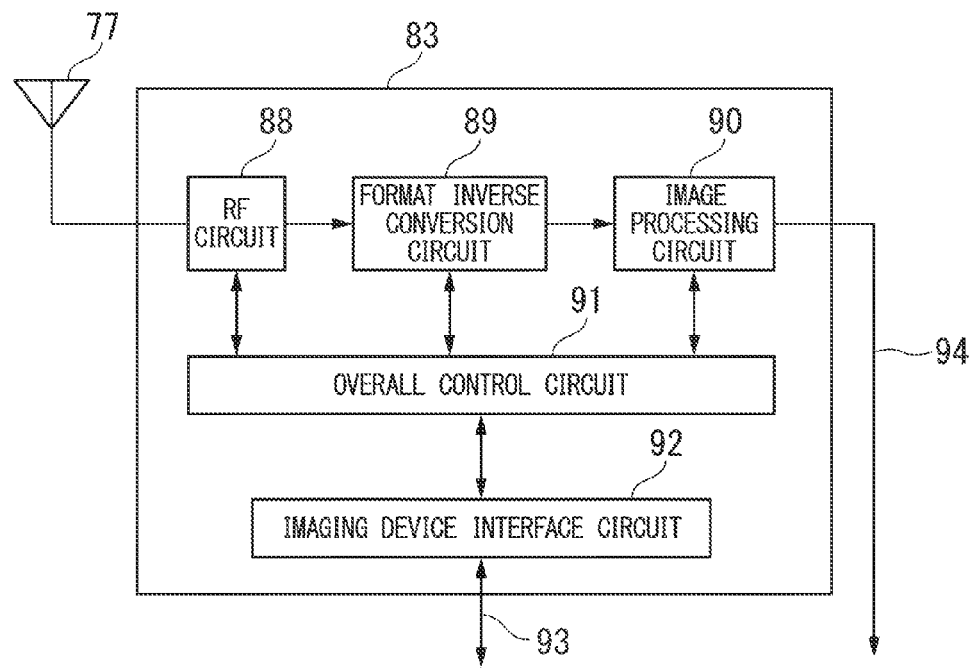
FIG. 18 is a block diagram showing the configuration of a reception device included in the imaging display system according to the third embodiment of the present invention.

A configuration of the reception device 83 will be described using FIG. 18. The reception device 83 includes an RF circuit 88 (a communication unit), a format inverse conversion circuit 89, an image processing circuit 90 (an image processing unit, an adjustment unit, an output unit), an overall control circuit 91, and an imaging device interface circuit 92. The configuration of the reception device 83 is a configuration in which the image processing circuit 90 that performs image processing on received captured image is added to the configuration of the reception device 10 of the first embodiment. The image processing circuit 90 is disposed on the back side of the format inverse conversion circuit 89, and performs image processing in accordance with content set by the overall control circuit 91 and outputs images after processing to the display processing device 84 as a received image signal 94. The configuration of the image processing circuit 90 is the same as that shown in FIG. 8. A reception device control signal 93 corresponds to the reception device control signal 47 of FIG. 7. The received image signal 94 corresponds to the received image signal 48 of FIG. 7. The configuration of the reception device 78 is the same as that of the reception device 83.

Figure 19:
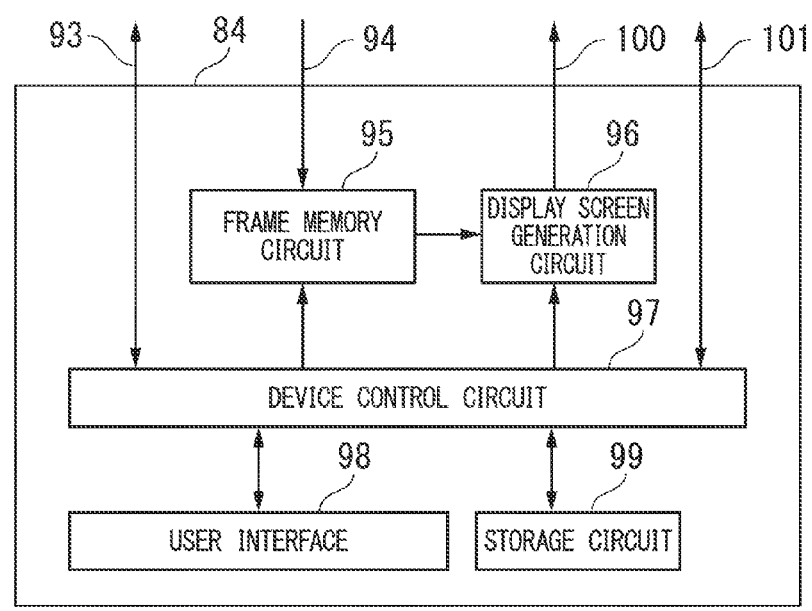
FIG. 19 is a block diagram showing a display processing device included in the imaging display system according to the third embodiment of the present invention.

A configuration of the display processing device 84 will be described using FIG. 19. The display processing device 84 includes a frame memory circuit 95, a display screen generation circuit 96, a device control circuit 97, a user interface 98, and a storage circuit 99. The configuration of the display processing device 84 is substantially the same as that of the display processing device 64 of the second embodiment, but is different therefrom in that a monitor information notifying signal 101 that enables communication between the device control circuit 97 and the monitor 85 is added. The reception device control signal 93 corresponds to the reception device control signal 74 of FIG. 13. The received image signal 94 corresponds to the received image signal 75 of FIG. 13. A display signal 100 corresponds to the display signal 76 of FIG. 13.

The monitor information notifying signal 101 is a signal for notifying the display processing device 84 of a display characteristic of the monitor 85. The display characteristic of the monitor 85 notified of by the monitor information notifying signal 101 is output to the reception device 83 as the reception device control signal 93, wirelessly transmitted from the reception device 83 to the remote controller 87, and then used at the time of generating an image quality adjustment target value.

Next, using FIGS. 20 to 24, image quality adjustment performed by the image processing circuits of the transmission device 4, the transmission device 61, the reception device 78, and the reception device 83 will be described. The image quality adjustment in the transmission device 4 and the transmission device 61 is performed by adjusting the qualities of the first captured image and the second captured image so that the qualities of the first captured image and the second captured image become the same as each other corresponding to a standard imaging characteristic value designated by the remote controller 87. The image quality adjustment in the reception device 78 and the reception device 83 is performed by adjusting the qualities of the first captured image and the second captured image so that the qualities of the first captured image and the second captured image received from the transmission device 4 and the transmission device 61 become qualities for each user corresponding to image quality adjustment target values designated by the remote controller 87.

First, image processing performed by the transmission device 4 and the transmission device 61 will be described. The image processing circuits in the transmission device 4 and the transmission device 61 decide adjustment values of a color gain, a hue angle, gamma, and a frequency characteristic based on imaging characteristic values of the connected imaging devices and standard imaging characteristic value, and set the adjustment values in each circuit. FIG. 20 shows the standard imaging characteristic values. The standard imaging characteristic values are appropriately decided as representative values of the imaging devices used in the imaging display system of the present embodiment. Since imaging characteristic values of the first imaging device 2 and the imaging device 59 are the same as those shown in FIG. 14 described in the second embodiment, the adjustment values of image processing performed by the transmission device 4 and the transmission device 61 are the values shown in FIG. 21.

In the case of the transmission device 4, for example, with regard to the color gain, the standard imaging characteristic value is 1.0, and the imaging characteristic value is 1.1, and thus the image quality adjustment value is 0.91 (=1.0/1.1). Likewise, with regard to the hue angle, the standard imaging characteristic value is 0 degrees, and the imaging characteristic value is +10 degrees, and thus the image quality adjustment value is −10 degrees.

Since the method for deciding the adjustment values of the gamma and the frequency characteristic is also the same as the method described in the second embodiment, and a description thereof will be omitted here.

Next, a method for deciding an imaging quality adjustment target value and image quality adjustment performed by the image processing circuits of the reception device 78 and the reception device 83 using the image quality adjustment target value will be described. First, the method for deciding an imaging quality adjustment target value will be described. An image quality adjustment target value is generated using adjustment values of the image processing circuits at the time when the adjustment values of the image processing circuits of the reception devices are adjusted in the state in which users observe captured images received from the imaging devices using the monitor 80 or the monitor 85 and thereby the qualities of the captured images being displayed become preferred image qualities, a display characteristic of a monitor in use, and standard imaging characteristic values.

At the time of generating image quality adjustment target values, the adjustment values of the image processing circuits and the display characteristic of the monitor are transmitted from the reception devices connected to the monitor in use to the remote controller 87, and accordingly, the image quality adjustment target values are generated by the remote controller 87. Hereinafter, a case in which a user whose ID is MD1 observes the first captured image received from the imaging device 2 on the monitor 80, the adjustment values of the image processing circuit of the reception device 78 are values indicated for RX_e of FIG. 24, and the quality of the first captured image wirelessly transmitted from the transmission device 4 is adjusted to be the image quality corresponding to the standard imaging characteristic value and then the display characteristic values of the monitor 80 are values indicated for DS_e of FIG. 23 will be described.

With regard to the color gain, the standard imaging characteristic value is 1.0, the display characteristic is 0.8, and the adjustment value is 1.13, and thus the image quality adjustment target value is 0.9 (=1.0×0.8×1.13). Likewise, with regard to the hue angle, the standard imaging characteristic value is 0 degrees, the display characteristic is 0 degrees, and the adjustment value is +5 degrees, and thus the image quality adjustment target value is +5 degrees (=0+0+5). With regard to gamma, the standard imaging characteristic value is 0.45, the display characteristic is 2.2, and the adjustment value is 1.11, and thus the image quality adjustment target value is 1.1 (=0.45×2.2×1.11). With regard to the frequency characteristic, the standard imaging characteristic values are 1, 1, 1, 1, 1.2, and 1, the display characteristic values are 1, 1, 1, 1.2, 1.2, and 1, and the adjustment values are 1, 1, 1, 0.83, 0.83, and 1.1, and thus the image quality adjustment target values are 1, 1, 1, 1, 1.2, and 1.1. As described above, the image quality adjustment target values show characteristics of a finally obtained image quality by reflecting the imaging characteristics of the imaging devices used at the time of generating the values and the display characteristic of the monitor. FIG. 22 shows an example of image quality adjustment target values of each user generated in the procedure described above.

Next, image quality adjustment performed by the image processing circuits of the reception device 78 and the reception device 83 using image quality adjustment target values will be described. Hereinafter, an example in which captured images are displayed on the monitor 85 with the image quality of the image quality adjustment target values for which the user ID of FIG. 22 is MD2 will be described. Adjustment values of the image processing circuit 90 of the reception device 83 are adjustment values that enable the captured images which are adjusted so as to have an image quality corresponding to a standard imaging characteristic to be displayed on the monitor 85 having the display characteristic shown in FIG. 23, with an image quality corresponding to the image quality adjustment target values of MD2 shown in FIG. 22.

With regard to the color gain, the standard imaging characteristic value is 1.0, the display characteristic is 0.9, and the image quality adjustment target value is 1.0, and thus the adjustment value is 1.11 (=1.0/(1.0×0.9)). With regard to the hue angle, the standard imaging characteristic value is 0 degrees, the display characteristic is 0 degrees, and the image quality adjustment target value is −10 degrees, and thus the adjustment value is −10 degrees (=0−0−10). With regard to gamma, the standard imaging characteristic value is 0.45, the display characteristic is 1.8, and the image quality adjustment target value is 1.0, and thus the adjustment value is 1.23 (=1.0/(0.45×1.8)). With regard to the frequency characteristic, the standard imaging characteristic values are 1, 1, 1, 1, 1.2, and 1, the display characteristic values are 1, 1, 1, 1.2, 1.3, and 1, and the image quality adjustment target values are 1, 1, 1, 1.2, 1.3, and 1, and thus, the adjustment values are 1, 1, 1, 0.83, 1, and 1.

An adjustment value control circuit in the image processing circuit 90 of the reception device 83 decides the adjustment values of the color gain, the hue angle, the gamma, and the frequency characteristic based on the standard imaging characteristic values, the display characteristics, and the image quality adjustment target values, and sets the adjustment values in each circuit. As the image processing circuit 90 performs image processing using the adjustment values, the captured images received from the imaging device 2 and the imaging device 59 are displayed on the monitor 85 with the image quality corresponding to the image quality adjustment target values of MD2 shown in FIG. 22.

As described above, according to the present embodiment, when the adjustment values are adjusted so as to reduce the difference in image qualities caused by imaging characteristics of the imaging devices, the adjustment values of the image processing circuit 35 of the transmission device 4 are adjusted based on the imaging characteristic values and the standard imaging characteristic values of the imaging device 2, and the adjustment values of the image processing circuit of the transmission device 61 are adjusted based on the imaging characteristic values and the standard imaging characteristic values of the imaging device 59, and accordingly, the difference in the qualities of images displayed on the same monitor can be reduced regardless of the imaging devices to be used.

In addition, by adjusting the adjustment values of the image processing circuits of the reception device 78 and the reception device 83 based on standard imaging characteristic values, a display characteristic, and image quality adjustment target values, images can be displayed with an image quality corresponding to image quality adjustment target values of each user regardless of a monitor to be used.

The aforementioned embodiment and each modification may be properly combined.

The invention is not limited by the above description, and is limited only by the scope of the appended claims.

What is claimed is:
1. A moving image display system comprising:
   a first imaging device including
      a first moving image generator which images a subject and generates first moving image data, and
      a moving image transmission device which at least wirelessly transmits the first moving image data obtained by the first image generator; and
   a second imaging device including
      a second moving image generator which images the subject and generates second moving image data,
      a moving image reception device which at least wirelessly receives the wirelessly transmitted first image data; and
      a display device which displays
         a first moving image based on the first moving image data wirelessly received by the image reception device and
         a second moving image based on the second moving image data output from the second moving image generator thereon,
   wherein the moving image reception device includes a first communication circuit which wirelessly transmits a second imaging characteristic parameter of the second moving image generator of the second imaging device to the moving image transmission device,
   wherein the moving image transmission device includes:
      an input circuit to which a first imaging characteristic parameter of the first moving image generator and the first moving image data are input;
      a second communication circuit which wirelessly receives the second imaging characteristic parameter of the second moving image generator;
      an adjustment circuit which generates an image processing parameter based on the first imaging characteristic parameter of the first moving image generator and the second imaging characteristic parameter of the second moving image generator, and reduces differences in image quality caused by imaging characteristics of each of the moving image generators, and an image processing circuit which performs moving image processing on the first moving image data input to the input circuit based on the image processing parameter generated by the adjustment circuit, and wherein the imaging characteristic parameter and the image processing parameter refer to one of color gain, hue angle, gamma, and frequency characteristic.

2. The moving image display system according to claim 1, wherein the second communication circuit wirelessly receives an adjustment target parameter of the quality of an image to be displayed on the display device.

3. The moving image display system according to claim 1, wherein the second communication circuit wirelessly receives a standard imaging characteristic parameter designated in advance as an index parameter.

4. The moving image display system according to claim 1, wherein the second communication circuit wirelessly receives an index parameter from the moving image reception device.

5. The moving image display system according to claim 1, wherein the second communication circuit wirelessly receives an index parameter from a control device which controls wireless connection of the moving image transmission device to the moving image reception device.

6. The moving image display system according to claim 1, wherein the adjustment circuit generates the image processing parameter based on a value obtained by dividing an index parameter by the imaging characteristic parameter.

* * * * *